United States Patent
Baysal et al.

(10) Patent No.: US 6,468,789 B1
(45) Date of Patent: Oct. 22, 2002

(54) OXYGEN SENSING AND HYPOXIC SELECTION FOR TUMORS

(75) Inventors: Bora E. Baysal; Robert E. Ferrell; Bernie J. Devlin; Joan E. Willett-Brozick, all of Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/496,632

(22) Filed: Feb. 2, 2000

(51) Int. Cl.[7] .......................... C12N 15/00; C12N 9/02; C12N 15/63; C12P 21/06; C07H 21/04

(52) U.S. Cl. ................... 435/320.1; 435/69.1; 435/455; 435/468; 435/471; 435/325; 435/185; 536/23.2; 536/24.31

(58) Field of Search .................... 514/44; 435/320.1, 435/455, 69.1, 325, 468, 471, 189, 419; 536/23.1, 23.2, 24.31

(56) References Cited

U.S. PATENT DOCUMENTS

| 5,827,711 A | * 10/1998 | Lal et al. ..................... 435/191 |
| 5,922,590 A | 7/1999 | Baylin et al. ............ 435/232.3 |
| 5,989,885 A | 11/1999 | Teng et al. .................. 435/194 |

OTHER PUBLICATIONS

Eck et al., Gene based therapy, 1996, Goodman and Gilman's The Pharmacological Basis of Therapeutics, pp. 77–101.*
Wivel, MD et al., Methods of gene delivery, 1998, Gene Therapy, vol. 12, pp. 483500.*
Deonarain, Ligand–targeted receptor–mediated vectors for gene delivery, 1998, Exp. Opin. Ther. Patents, vol. 8, pp. 53–69.*
Verma et al., Gene therapy–promises, problems and prospects, 1997, Nature, vol. 389, pp. 239–242.*
Ngo et. al.; Computational Complexity, Protein Structure Prediction, and the Levinthal Paradox, 1994, In The Protein Folding Problem and Teritary Structure Prediction, pp. 491–495.*
Rudinger; Characteristics of the amino acids as components of a peptide hormone sequence, 1976, In Peptide Hormones, pp. 1–7.*
Wivel, N.A. & Wilson, J.M. Methods of gene delivery. Hematol. Oncol. Clin. North Am. 12:483–501, 1998.*
Deonarain, M.P. Ligand–targeted receptor–mediated vectors for gene delivery. Exp. Opin. Ther. Patents 8:53–69, 1998.*
Verma, I.M. & Somia, N. Gene therapy—promises, problems and prospects. Nature 389:239–242, 1997.*
Eck, S.L. & Wilson, J.M. Gene–based therapy in Goodman & Gilman's The pharmacological basis of therapeutics, Ninth edition, pp. 77–101, 1996.*

Hirawake, H. et al. Cytochrome b in human complex II (succinate–ubiquinone oxidoreductase): cDNA cloning of the components in liver mitochondria and chromosome assignment of the genes for the large (SDHC) and small (SDHD) subunits to 1q21 and 11q23. Cytogenet. Cell Genet. 1997; 79: 132–138.

Hirawake, H. et al. Characterization of the human SDHD gene encoding the small subunit of cytochrome b (cybS) in mitochondrial succinate–ubiquinone oxidoreductase. Biochim et Biophys Acta. 1999; 1412:295–300.

Van Der May, A.G.L. et al. Genomic Imprinting in hereditary glomus tumours: evidence for new genetic theory. Lancet. 1989; Dec 2;2(8675):1291–1294..

Morison, I.M. et al. A catalogue of imprinted genes and parent–of–origin effects in humans and animals. Hum Mol Genet 1998; 7(10):1599–1609.

Baysal, B.E. et al. A high–resolution STS, EST, and gene–based physical map of the hereditary paraganglioma region on chromosome 11q23. Genomics. 1997; 44:214–221.

Deloukas, P. et al. A physical map of 30,000 human genes. Science. 1998; 282:744–746.

Scheffler I.E. Molecular genetics of succinate:quinone oxidoreductase in eukaryotes. Prog Nucleic Acid Res Mol Biol. 1998; 60:267–315.

Chandel, N.S. et al. Mitochondrial reactive oxygen species trigger hypoxia–induced transcription. Proc Natl Acad Sci USA 1998; 95: 11715–11720.

Naoaki, I. et al. A mutation in succinate dehydrogenase cytochrome b causes oxidative stress and aging in nematodes. Nature 1998: 394(6694):694–697.

Zhu, H. et al. Oxygen sensing and signaling: impact on the regulation of physiologically important genes. Respir Physiol 1999; 115: 239–247.

Semenza, G.L. Perspectives on oxygen sensing. Cell 1999; 98: 281–284.

Bunn, H.F. Oxygen sensing and molecular adaptation to hypoxia. Physiol Rev 1996; 76(3):839–885.

(List continued on next page.)

*Primary Examiner*—Dave T. Nguyen
*Assistant Examiner*—Quang Nguyen
(74) *Attorney, Agent, or Firm*—Reed Smith LLP

(57) ABSTRACT

The present invention is directed to oxygen sensing. The present invention provides methods for correcting (or providing for) oxygen sensing in cells. Preferably, the methods involve supplying the SDHD gene or cybS protein, or any of the other components of the mitochondrial complex II cytochrome b oxygen sensing complex in an amount which restores oxygen sensing to affected cells, and thus facilitates normoxic conditions. More specifically, the present invention relates to mutations in the SDHD gene in human cancers and their use in the diagnosis and prognosis of mammalian cancer.

9 Claims, 4 Drawing Sheets

OTHER PUBLICATIONS

Gonzalez, C. et al. Carotid body chemoreceptors: from natural stimuli to sensory discharges. Physiol Rev 1994; 74(4): 829–898.
Arias–Stella, J. et al. Chronic hypoxia and chemodectomas in bovines at high altitudes. Arch Pathol Lab Med 1976; 100: 636–639.
Arias–Stella, J. et al. Chief cell hyperplasis in the human carotid body at high altitudes. Human Path 1976; 7(1): 361–373.
Edwards, C. et al. The carotid body in animals at high altitude. J Path 1971; 104:231–238.
Saldana, M.J. et al. High altitude hypoxia and chemodectomas. Human Path 1973; 4(2): 251–263.
Bee, D. et al. Division of type I and endothelial cells in the hypoxia rat carotid body. Acta Anat 1986; 126: 226–229.
Nurse, C.A. et al. Role of basic FGF and oxygen in control of proliferation, survival, and neuronal differentiation in carotid body chromafin cells. Dev Biol 1997; 184: 197–206.
Lack, E.E. Hyperplasia of vagal and carotid body paraganglia in patients with chronic hypoxemia. Amer J Pathol 1978; 91(3): 497–507.
Lack, E.E. et al. Carotid body hyperplasia in cystic fibrosis and cyanotic heart disease. Amer J Pathol 1985; 119(2):301–314.
Lack, E.E. et al. Paragangliomas of the head and neck region. Human Pathol 1979; 10(2): 191–218.
Stiller, D. et al. Jugular body tumors:hyperplasias or true neoplasms? Virchows Arch A Path Anat and Histol 1975; 365:163–177.
Heutink, P. et al. A gene subject to genomic imprinting and responsible for hereditary paragangliomas maps to chromosome 11q23–qter. Hum Mole Genet 1992; 1(1): 7–10.
Heutink, P. et al. Further localization of the gene for hereditary paragangliomas and evidence for linkage in unrelated families. Eur J Hum Genet 1994; 2:148–158.
Milunsky, J. et al. Familial paragangliomas: linkage to chromosome 11q23 and clinical implications. Am J Med Genet 1997; 72:66–70.
Baysal, B.E. et al. Fine mapping of an imprinted gene for familial nonchromaffin paragangliomas, on chromosome 11q23. Am J Hum Genet 1997; 60:121–132.
Baysal, B.E. et al. Repositioning the hereditary paraganlioma critical region on chromosome band 11q23. Hum Genet 1999; 104:219–225.
Baysal, B.E. et al. Genomic organization and precise physical location of protein phosphatase 2A regulatory subunit A beta isoform gene on chromosome band 11q23. Gene 1998; 217:107–116.
van Schothorst, E.M. et al. Founder effect at PGL1 in hereditary head and neck paraganliomas families from the Netherlands. Am J Hum Genet 1998; 63:468–473.
Nakamura, K. et al. Two hydophobic subunits are essential for the heme b ligation and functional assembly of complex II (succinate–ubiquinone oxidoreductase) from *Escherichia coli*. J Biol Chem 1996; 271(1): 521–527.
Vibat, C.R.T. et al. Localization of histidine residues responsible for heme axial ligation in cytochrome $b_{556}$ of complex II (succinate: ubiquinone oxidoreductase) in *Escherichia coli*. Biochem 1998, 37: 4148–4159.
Shenoy, S.K. et al. Identification of quinone–binding and heme–ligating residues of the smallest membrane–anchoring subunit (QPs3) of bovine heart mitochondrial succinate:ubiquinone reductase. J Biol Chem 1999; 274(13): 8717–8722.
Chomczynski, P. et al. Single–step method of RNA isolation by acid guanidinium thiocyanate–phenol–chloroform extraction. Anal Biochem 1987; 162: 156–159.
Vu, T.H. et al. Imprinting of the Angelman syndrome gene, UBE3A, is restricted to brain. Nature Genet 1997; 17:12–13.
Devilee, P. et al. Allelotype of head and neck paragangliomas:allelic imbalance is confined to the long arm of chromosome 11, the site of the predisposing locus PGL. Genes Chromosom Cancer 1994; 11:71–78.
Maxwell, P.H. et al. The tumor suppressor protein VHL targets hypoxia–inducible factors for oxygen–dependent proteolysis. Nature 1999; 399:271–275.
van Schothorst, E.M. et al. Paragangliomas of the head and neck region show complete loss of heterozygosity at 11q22–q23 in chief cells and the flow–sorted DNA aneuploid fraction. Hum Pathol 1998; 29(10):1045–1049.
Vaupel, P. et al. Oxygenation of human tumors: the Mainz experience. Strahlenther Onkol 1998; 174(4): 6–12.
Graeber, T.G. et al. Hypoxia–mediated selection of cells with diminished apoptotic potential in solid tumours. Nature 1996; 379:88–91.
Koreth, J. et al. Chromosomes, 11Q and cancer: a review. J Pathol 1999; 187:28–38.
Farr, J.E. et al. Search for imprinting effects in the hereditary paraganglioma critical region on chromosome band 11q23:allelic expression analysis of PPP2R1B, POU2AF1, D11S966E and methylation analysis of two NotI sites associated with novel genes. Am J Hum Genet 1999, Suppl S, 65: (4) A271.
Morelli, L. et al. Effect of acute and chronic cobalt administration on carotid body chemoreceptors responses. Sci total Environ 1994, 150:215–16.

* cited by examiner

```
                                                            ↓   1          2
H.sapiens    MAVLWRLSAVCGALGGRALLLRTPVVR---PAHISAFLQDRPIPEWCGVQHIHLSPSHHS
B.taurus     -MALWRLSVLCGAKEGRALFLRTPVVR---PALVSAFLQDRPAQGWCGTQHIHLSPSHHS
A.suum       ------MLSAVRRAIPLSARILRTSLIQRCAGATSAAVTGAAPPQFDPIAAEKGFKPLHSH
C.elegans    -----------MAASLRHMAHFQKALLVAR--SAPRISTIVRATSTLNDGASKV---PDHS-
                         *                                    *      *    *

3                   4               5
H.sapiens    GSKAASLHWTSERVVSVLLLGLLPAAYLNPCSAMDYSLAAALTLHGHWGLGQVVTDY---
B.taurus     GSKAASLHWTGERVVSVLLLGLLPAAYLNPCSAMDYSLAATLTLHSHWGIGQVVTDY---
A.suum       GT----LFKIERYFAAAMVPLIPAAYFIHGREMDLCLALALTLHVHWGVWGVVNDYGRP
C.elegans    -------MHFKLERLWAVGMLPILPASYFIHGPVMDAVLTLHIHWGIHGVVYDYARP
                   *  *          *    *   *      * * *   *  **   ***  **

H.sapiens    -VHGDALQKAAKAGLLALSALTFAGLCYFNYHDVGICKAVAMLWKL
B.taurus     -VHGDAVQKAAKTGLLVLSAFTFAGLCYFNYHDVGICKAVAMLWKL
A.suum       FVLGDTLAAAVRVGAYIFTACLLAGLLYFNEHDVGLTRAFEMVWEL
C.elegans    YVIGEAAAKAAHVGVYLITGLLLGALLHFNTNDVGITKAFELVFSL
                 *    *  *        *     **  *** *   * *   *
```

FIG. 3

OXYGEN SENSING AND HYPOXIC SELECTION FOR TUMORS

FIELD OF THE INVENTION

Generally, the present invention relates to the discovery and utilization of a biological oxygen sensor in the diagnosis, prognosis, prevention and/or treatment of undesirable biological states. More particularly, the present invention relates to improving or restoring cellular and/or tissue oxygenation, preferably to benefit undesirable states associated with tissue oxygen sensing. The present invention generally contemplates devices, drugs, or treatment methodologies involved with tissue oxygenation, especially in tissue that would benefit from such treatment. The methodologies contemplated herein include gene therapy, protein replacement therapy, and protein mimetics.

BACKGROUND OF THE INVENTION

It is postulated that as certain tumors enlarge, tissue often outgrows its oxygen and nutrient supply because of an inadequate network of functioning blood vessels and capillaries. Although cells deprived of oxygen and nutrients may ultimately die, at any given time a tumor cell may produce viable hypoxic cells that are viable in hypoxic environments. Hypoxic cells, although alive, have very low oxygen concentrations because of their remoteness from the blood vessels.

Hypoxia appears to contribute to resistance to radiotherapy and chemotherapy in many tumors. Hypoxia can also be an independent poor prognostic factor in many cancers, e.g. cervical cancer. Hypoxic stimulation provides environmental pressure for further tumor cell selection, growth and progression to more aggressive stages. This is referred to as hypoxia-mediated selection. For example, p53 mutations found in solid cancers, are proposed to be the result of such hypoxia-mediated selection. Mutations in p53 are postulated to confer resistance to apoptosis, a cellular defense mechanism that leads to cell death.

Hypoxic conditions increase a tumor's resistance to conventional treatment in a number of ways. When chemotherapeutic agents are administered to patients, the agents are carried through the functioning blood vessels and capillaries to the target tissue. Because hypoxic tissue lacks a fully functioning blood supply network, chemotherapeutic drugs may never reach the hypoxic cells; instead, intervening cells scavenge the drug. The result is that the hypoxic cells survive and recurrence of the tumor is possible.

Hypoxia also hinders the effectiveness of radiation therapy, especially of neoplasms. Radiation treatment is most effective in destroying oxygen containing cells because oxygen is an excellent radiation sensitizer. The presence of hypoxic cells impedes this treatment. Therefore, hypoxic cells are more likely to survive radiation therapy and eventually lead to the reappearance of the tumor. The importance of hypoxic cells in limiting radiation responsiveness in animal tumors is well known. In addition to its role in tumorigenesis, hypoxia is a factor in the pathogenesis of major causes of mortality including myocardial ischemia, stroke, cancer, and chronic lung disease. Hypoxia plays a role in many diverse disease states.

One of the most important goals in oncology is the identification and elimination of treatment resistant cells; hypoxic cells being the most familiar examples of this type of cell. Surprisingly the carotid body in mammals may provide insight into these treatment resistant cells. In mammals, the carotid body (CB) appears to play a major role in acute adaptation to hypoxia by stimulating the cardiopulmonary system. Chronic exposure of mammals to hypoxic conditions, observed for example in humans living at high altitudes, induces hyperplastic/anaplastic growth in the carotid body. Similar hyperplastic/anaplastic growth in the CB is observed in individuals with chronic arterial hypoxemia, such as cyanotic heart and chronic lung diseases. The carotid body is a highly vascular small organ located at the bifurcation of the common carotid artery in the neck and is a chemoreceptive organ involved in sensing oxygen levels in the blood.

Stimulation of the cardiopulmonary system results in increased blood flow and subsequent increase in oxygenation of tissue. At the cellular level, this sequence is thought to involve a hypoxia-inducible transcription factor (HIF-1), activation of which leads to a systemic response. The systemic response includes an increase in red cell mass, stimulation of new blood vessel growth, and increased ventilation.

SUMMARY OF THE INVENTION

As will be more fully described herein, it appears that the mitochondrial complex II cytochrome b is an important (potentially primary) oxygen sensor in mammalian cells. The protein subunits of mitochondria complex II cytochrome b appears to be involved in oxygen sensing and provide a novel genetic and pharmacological target. Therapies designed to amplify adaptive responses to hypoxia and, conversely, to inhibit these responses in cancer cells are now viable. A comprehensive understanding of the mitochondrial complex II cytochrome b also provides a target for effective therapies for neurodegenerative diseases such as Parkinson's and Alzheimer's.

One aspect of the present invention is a method for treating diseased states especially in mammals. These diseased states are preferably associated directly or indirectly with tissue oxygenation. Accordingly, one embodiment of the present invention describes a method of treating a diseased state in a human comprised of identifying hypoxic cells, and supplying an oxygen sensor to said cells. It may also be preferable to create a hyperbaric environment for the cells to which the oxygen sensor is provided.

The present invention further provides methods for correcting and/or augmenting oxygen sensing defects in cells. Preferred methods involve supplying the SDHD gene or cybS protein, or any of the other components of the mitochondrial complex II cytochrome b oxygen sensing complex in an amount which restores or imposes oxygen sensing to affected or surrounding cells, and thus facilitates normoxic conditions.

An additional aspect of the invention relates to creating hypoxic cells by incorporating missense or nonsense mutations in an SDHD gene and supplying such a mutated SDHD gene to desired cells.

Further, the invention relates to the PGL1 locus, cloning vectors, expression systems and recombinant cells comprising the SDHD coding sequence, the PGL1 locus, and variations thereof.

A further embodiment of the present invention provides nucleic acid probes complementary to the SDHD gene as well as to SDHD mutants. A related aspect of the invention includes DNA primers for amplification of nucleic acid fragments of the PGL1 locus.

Additionally, the present invention provides methods and kits for diagnosing diseased states in mammals including PGL, and those relating to decreased tissue oxygenation or oxygen stress.

An alternative embodiment of the present invention provides a method of treating a diseased state preferably a nuerodegenerative disease in a human by supplying autologous carotid body cells to oxidatively stressed regions.

Yet another feature of the present invention resides in an expression system which includes a DNA sequence, said DNA sequence corresponding to a portion of PGL1 locus. The expression system is a recombinant host cell transformed with said DNA sequence. The portion of PGLL locus corresponds to SEQ ID NO:1. Alternatively, the portion of PGL1 locus corresponds to SEQ ID NO:2. The DNA sequence includes a nucleotide analog which is incapable of being methylated.

Another aspect of the present invention resides in an isolated DNA sequence comprised of a sequence selected from the group consisting of SEQ ID NO:1, SEQ ID NO:2 and portions thereof, wherein the sequence includes a mutation selected from the group consisting of nonsense, missense and deletion mutation Alternatively, the mutation is a mutation in SEQ ID NO:1 selected from the group consisting of: a T at nucleotide base number 106 of SEQ ID NO:1; a T at nucleotide base number 112 of SEQ ID NO:1; a T at nucleotide base number 242 of SEQ ID NO:1; and a T at nucleotide base number 305 of SEQ ID NO:1.

Yet another feature of the present invention resides in a method of treating a diseased state comprised of supplying a biological oxygen sensor to a patient in need thereof. The biological sensor is a mitochondrial complex II protein. The mitochondrial complex II protein include a functional cybS subunit. The biological oxygen sensor includes a protein sequence corresponding to SEQ ID NO:3. The biological mitochondrial complex II protein includes a protein sequence corresponding to SEQ ID NO:3. The step of supplying a biological oxygen sensor includes supplying autologous carotid body cells to said patient. The disease may be a neurodegenerative disease. The biological oxygen sensor may be supplied in conjunction with a therapeutic treatment, said treatment being selected from the group consisting of radiation and chemotherapy. The biological oxygen sensor may be resistant to methylation.

The present invention broadly facilitates a number of useful treatments involving oxygen sensing or tissue oxygenation. The treatment may involve identifying hypoxic cells; supplying or restoring a biological oxygen sensor to the cells; and creating a hyperbaric environment for said cells having an oxygen sensor to thereby improve tissue oxygenation.

In one embodiment, the present invention utilizes the proliferative and oxygen sensing capabilities of CB cells by measuring the levels of mitochondrial complex II cytochrome b components (e.g. cybS or cybL. Such measurements may be useful in treating and monitoring patients with neurodegenerative diseases.

Under some circumstances it may be desirable to provide a method of treating a diseased state in an individual, comprising supplying a demethylating agent to tissue in need of such and agent, such that tissue oxygenation is improved. The present invention facilitates such a method, as well as an expression system wherein the isolated DNA contains a non-methylatable nucleotide analog. Further, recombinant host cells transformed with the above expression system are also provided by the present invention.

In addition to providing general treatments for diseased states, the present invention provides a method of augmenting a treatment by identifying hypoxic cells; supplying an oxygen sensor to said cells; and creating a hyperbaric environment for said cells having an oxygen sensor. Examples of the augmented treatment include chemotherapy, radiation therapy, tissue oxygenation, and supplying an oxygen sensor to said cells. Furthermore, these treatments may include the step of creating a hyperbaric environment for said cells having an oxygen sensor.

The present invention also involves the isolated DNAs sequences utilized in a replicative cloning vector which comprises the isolated DNA of the PGL1 locus, SEQ ID NO:1, or SEQ ID NO:2 and a replicon operative in a host cell. Additional embodiments include an expression system which comprises the isolated DNA of the PGL1 locus, SEQ ID NO:1 or SEQ ID NO:2, operably linked to suitable control sequences. Recombinant host cells can be transformed with the any of these replicative cloning vectors.

Various nucleic acid probes and primers of the present invention may also be useful in diagnostic and therapeutic techniques. Among these are a nucleic acid probe complementary to human SDHD gene as well as a nucleic acid probe complementary to human altered SDHD gene sequences wherein said nucleic acid probe hybridizes to a mutant SDHD gene under hybridization conditions which prevent hybridizing of said nucleic acid probe to a wild-type SDHD gene.

The present invention will also facilitate the amplification of segments of the PGL1 locus. Several methods providing for this amplification are described including: a pair of single-stranded DNA primers wherein use of said primers in a polymerase chain reaction results in amplification of an SDHD gene fragment, wherein the sequence of said primers is derived from the regions of the isolated DNA defined by SEQ ID NO:2. Similarly, the invention also provides for a pair of single-stranded DNA primers wherein use of said primers in a polymerase chain reaction results in amplification of an SDHD gene fragment, wherein the sequence of said primers is derived from the exon regions of the isolated DNA defined by SEQ ID NO:1.

In addition to the diagnostic methods detailed above, the present invention also provides kits for detecting SDHD mutations. One such kit for detection of SDHD mutations is one comprising: an oligonucleotide fragment from SEQ ID NO:2; and means for detecting said SDHD nucleic acids. An additional kit detects PGL comprising: a set of primers for detection of SDHD from SEQ ID NO:2; and means for detecting said SDHD nucleic acids.

BRIEF DESCRIPTION OF THE DRAWINGS

The present invention and its presently preferred embodiments will be better understood by way of reference to the detailed disclosure herebelow and to the accompanying drawings, wherein:

FIG. 3 is an alignment of cybS amino acid sequences from four eukaryotic multicellular organisms identified by BLASTP analysis of Swissprot database; *H. sapiens* (SEQ ID NO: 15), *B. Taurus* (SEQ ID NO: 16), *A. suum* (SEQ ID NO: 17) and *C. elegans* (SEQ ID NO: 18).

DETAILED DESCRIPTION OF THE PREFERRED EMBODIMENTS

Hereditary paraganglioma (PGL) is characterized by the development of benign, vascularized tumors in the head and neck. The most common tumor site is the carotid body (CB), a chemoreceptive organ that is involved in sensing oxygen levels in the blood. Several features of PGL, including its benign biological behavior, limited organ involvement, and histopathology are markedly similar to the features of hyperplastic/anaplastic growth seen in the CB of individuals with chronic arterial hypoxemia.

Histological analyses show hyperplasia/anaplasia of the CB chemoreceptor cells, which presumably results from sustained stimulation by hypobaric hypoxia. Experimental hypoxic conditions also result in CB enlargement and mitogenesis in rats. CB enlargement and hyperplasia are also observed in medical conditions with normobaric chronic arterial hypoxemia including cyanotic heart diseases and chronic lung diseases such as emphysema and cystic fibrosis. Thus, chronic hypoxic stimulation appears to be a common underlying factor leading to CB enlargement and cellular hyperplasia.

The remarkable mimicry of CB enlargement due to chronic hypoxic stimulation and PGL, including benign biological behavior, limited organ involvement, and similar histopathology led to the hypothesis that the genetic defect in PGL1 involves a critical component in the oxygen sensing and signaling pathway. Interestingly, many solid tumors, including lung, breast, colorectal, cervical, nasopharyngeal, ovary, stomach, bladder carcinomas and melanoma show somatic deletions encompassing the PGL1 gene region on chromosome 11q23. This consistent deletion pattern and the similarity between PGL and hyperplastic/anaplastic growth in the CB of chronically hypoxia-exposed individuals suggests that targeting of the hypoxia-inducing PGL1 gene provides a genetic means to attain intracellular hypoxic stimulation, which subsequently lead to the selection of a more aggressive sub-population of cancer cells.

Figure 2:
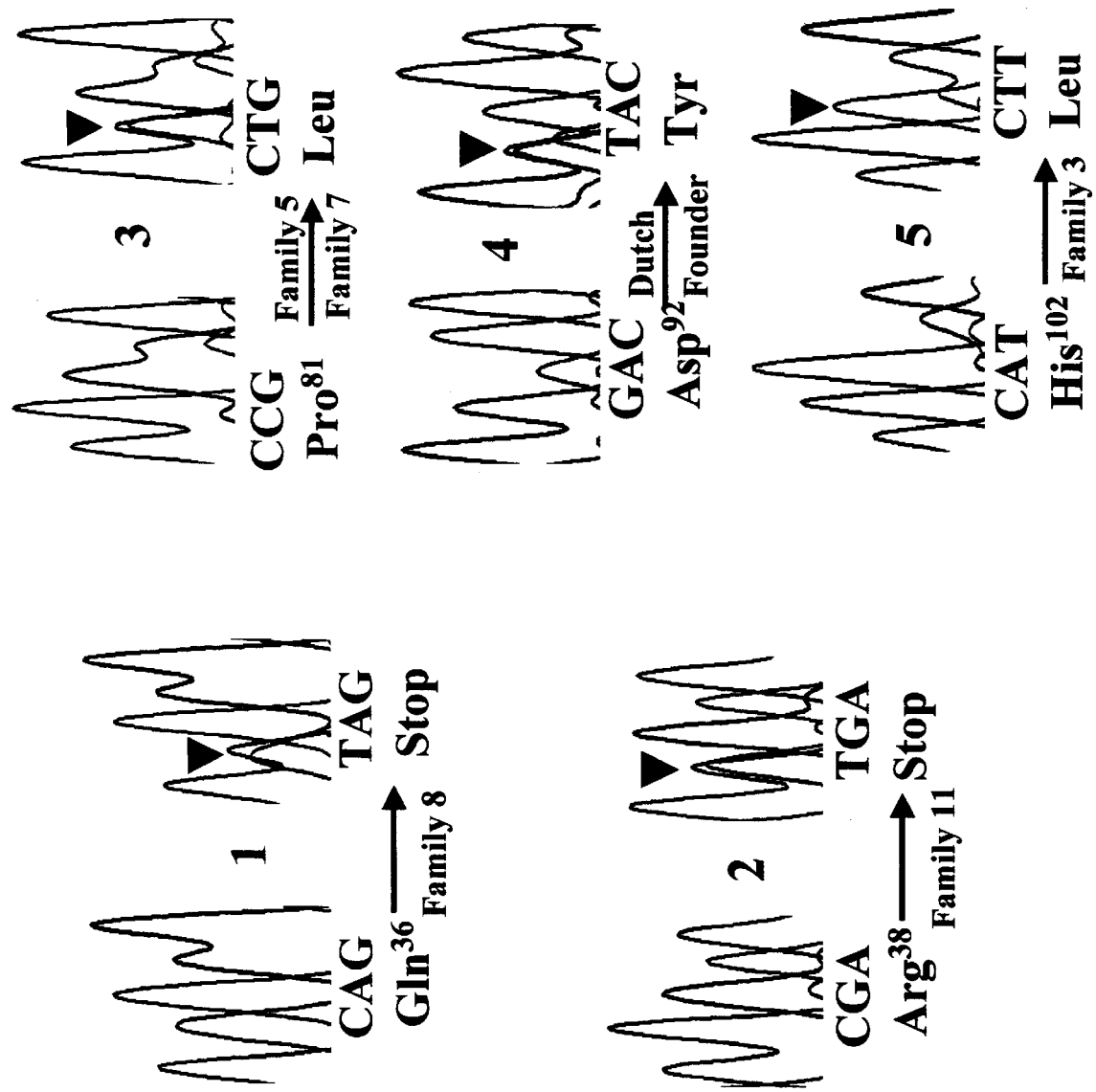
FIG. 2 shows the sequencing chromatograms with the alterations (arrow head) responsible for the four major PGL1 mutations. (The affected codons and the amino acids are depicted below the chromatograms)

Most cases of PGL are attributable to the PGL1 locus, at chromosome 11q23. Analysis of PGL1 families reveals germline mutations in SDHD. FIG. 2 shows the sequencing chromatograms with the alterations (arrow head) responsible for the five major PGL1 mutations. (The affected codons and the amino acids are depicted below the chromatograms.) SDHD encodes a mitochondrial respiratory chain protein which appears to be a mammalian heme-containing oxygen sensor. A wealth of independent biochemical and physiological evidence supports the presence of a mammalian heme-containing oxygen sensor, which is critically involved in triggering hypoxia-induced pathways such as Erythropoeitin production and CB chemoreceptor discharge. Although other heme-based bio-sensors have been identified, the mammalian oxygen sensor remains obscure. Functional and structural characterizations of mitochrondrial complex II cytochrome b are consistent with those of an oxygen sensor. First, it is a heme protein. Secondly, spectral measurements in the presence and absence of respiratory cytochrome inhibitors suggest a b-like cytochrome sensor in CB chemoreceptor cells and Erythropoeitin-producing cells. Thirdly, a mutation in the gene encoding cybL-homolog in *Caenorhabditis elegans* causes oxidative stress and premature aging, suggesting a critical role for cytochrome b in determining the formation of superoxide, a postulated downstream effector in the oxygen sensing and signaling pathway. Lastly, its mitochondrial location is consistent with recent evidence, which excludes a major oxygen-sensing role in pulmonary vasculature for NADPH oxidase, another candidate sensor located in the cytosolic membrane. Thus, mitochondrial complex II cytochrome b has all the hallmarks of a mammalian oxygen sensor.

PGL tumors display cellular hyperplasia/anaplasia without the requirement of a hypoxic environment or stimulation. Interestingly, for PGL1-linked families, mothers do not transmit the disease, suggesting an imprinted phenotype of SDHD. However, SDHD does not show imprinted expression in tested tissues. This inheritance pattern is observed in all confirmed PGL1 pedigrees, and suggests sex-specific epigenetic modification of PGL1 during gametogenesis consistent with genomic imprinting. This consistent inheritance pattern gives PGL a unique place among the known human genetic disorders with parent-of origin effects.

SDHD encodes the small subunit of cytochrome b (cybS) in succinate-ubiquinone oxidoreductase (mitochondrial complex II). Mitochondrial complex II is involved in the Krebs cycle and in the aerobic electron transport chain. It consists of four proteins: a flavoprotein and an iron-sulfur protein comprise the catalytic core, and the large subunit of cytochrome b (cybL) and the small subunit of cytochrome b (cybS) and cybS comprise the heme-protein cytochrome b, and anchor the catalytic subunits to the mitochondrial inner membrane. SDHD was evaluated as a candidate gene for PGL1 since it has been argued that the mitochondrial electron transport chain plays a role in oxygen sensing and signaling through reactive oxygen species production for which the cytochrome b in succinate-ubiquinone oxidoreductase could be critically involved.

Based on the phenotypic similarity between PGL and the CB's response to chronic hypoxia, it appears that cybS is a critical component of the oxygen-sensing system of paraganglionic tissue, and possibly all mammalian cells, and its loss leads to chronic hypoxic stimulation and cellular proliferation. Hypoxic stimulation has also been implicated as an etiologic factor in von Hippel-Lindau disease, which shows constitutive activation of hypoxia-inducible factor 1 (HIF-1). Normoxic conditions lead to oxidative modification and degradation of the alpha subunit of HIF-1, and prevents the activation of HIF-1. The activated HIF-1 stimulates the synthesis of erythropoietin (Epo), which increases red cell mass, vascular endothelial growth factor, which stimulates new blood vessel growth, and tyrosine hydroxylase, which is involved in the control of ventilation by the CB.

Currently, there are no molecular targets (e.g., sensors) available for improving tissue oxygenation and preventing or decreasing hypoxia. Hyperbaric oxygenation can be employed as an anti-neoplastic adjunct therapy in some cases. However, it is proffered herein that hyperbaric oxygen therapy is less likely to alleviate hypoxic stimulation absentan intact oxygen sensor. Delivery or correction of an oxygen sensor, e.g. the SDHD gene or the cybS protein, may help to achieve a better response to radiotherapy and to some chemotherapies. There is a generally recognized need for such a target which could provide means for diagnosis, treatment, and prevention of many conditions where tissue oxygenation is limited.

Because both cybS and cybL are indispensable for heme ligation, loss of normal cybS should prevent formation of functional cytochrome b. If cytochrome b were to play a rate-limiting, sensor role in the oxygen-sensing pathway under normoxemic conditions, then its loss could lead to chronic hypoxic activation of the pathway, which subsequently induces mitotic activity in CB chemoreceptive cells.

Figure 1:
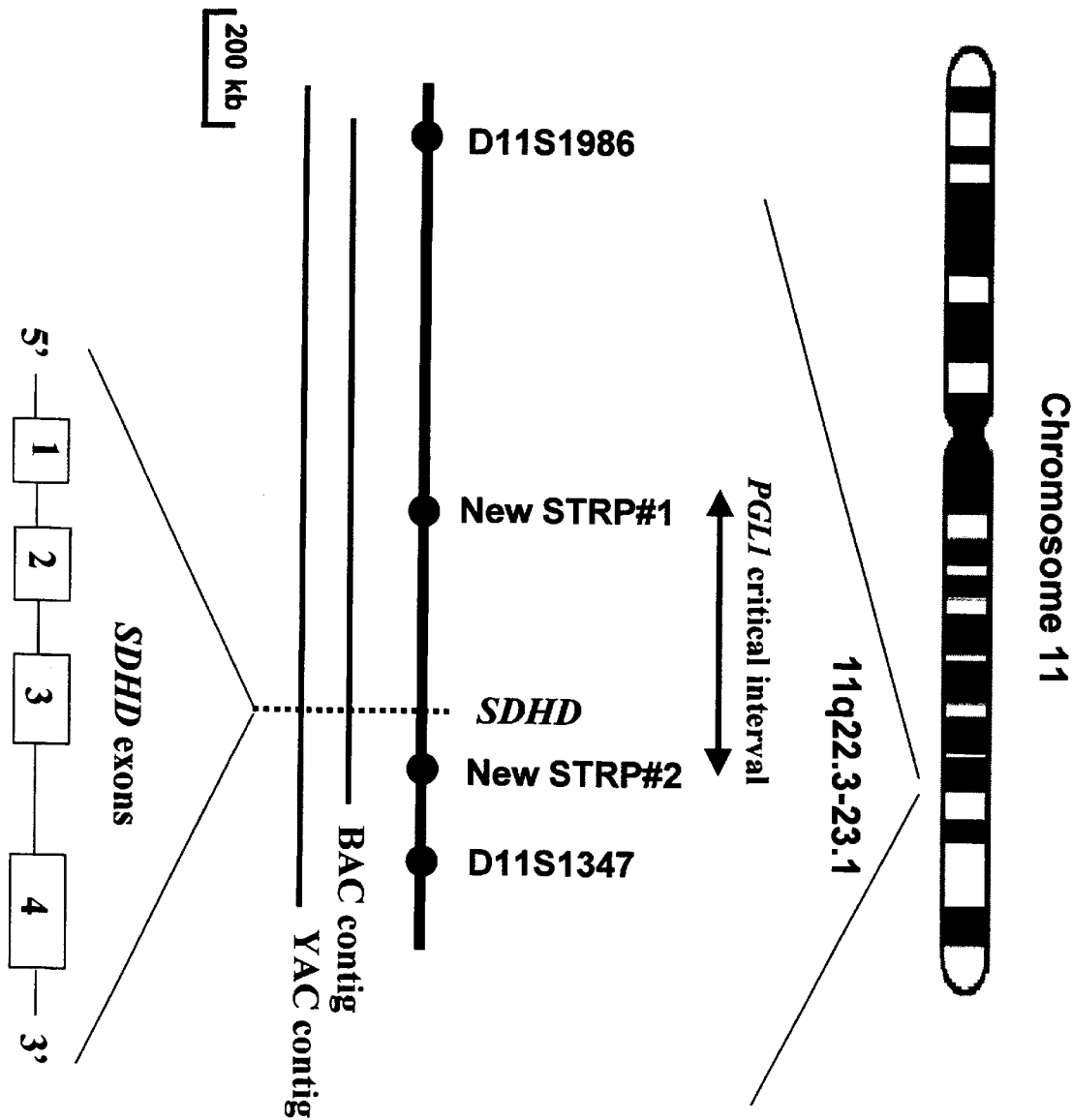
FIG. 1 is a map of the PGL1 critical region on chromosome band 11q23. (Exons are denoted with boxes, introns are denoted with horizontal lines)

PGL1 was localized to an approximately 1.5 Mb critical interval between D11S1986 and D11S1347. Bacterial artificial chromosome (BAC) and yeast artificial chromosome (YAC) contig construction and discovery of sixteen new simple tandem repeat polymorphisms (STRP) enabled further localization of PGL1 to an approximate 400 kb region flanked by the recombination breakpoints in families 5 and 12 as shown in FIG. 1.

Expressed sequence tag (EST)/gene content mapping of transcripts revealed a high density of transcripts both in the 400 kb PGL1 critical region and in its close vicinity. A database search using BLAST with one of the ESTs in the critical region, EST229158, identified a complete match to a genomic sequence (GENbank#AB026906) containing the exons of the succinate-ubiquinone oxidoreductase subunit D gene (SDHD). SDHD was previously mapped to chromosome band 11q23 by fluorescent in situ hybridization, and its genomic structure has been characterized (Hirawake, H. et al.) Biochimica et Biophysica Acta 1412 (1999) 295–300. The location of SDHD in the PGL1 critical region was determined by mapping it back to both the BAC and YAC contigs, and was found to be close to the telomeric exclusion border. SDHD spans over 19 kb at the genomic level, and its translated region consists of four exons of 52, 117, 145, and 163 bp as depicted in FIG. 1. The PCR primer sequences for the two new (CA)n STRP that flank the 400 kb critical interval size are as follows: STRP #1: 5'-AAACGCAGCAAGACCCTGTT-3' (SEQ ID NO:4) and 5'-AGGGGTTCATGACCATCCTA-3' (SEQ ID NO:5); STRP#2:5'-CATTTGTCCAGTTACCCGTA-3' (SEQ ID NO:6) and 5'-TATTGACTAATGGACACTGGAA-3' (SEQ ID NO:7). STRP#1 has five alleles in the 187–195 bp range. STRP#2 has four alleles in the 168–174 bp range. Both STRP are amplified using standard PCR conditions.

The primers for exon amplifications are as follows: 1F: 5'-TCAGGGTGGGAAGACCCCT-3'(SEQ ID NO:8); 2F: 5'-GATCATCCTAATGACTCTTTCC-3' (SEQ ID NO:9); 2R: 5'-AGCAGCAGCGATGGAGAGAA-3' (SEQ ID NO:10); 3F: 5'-CTTTTATGAATCTGGTCCTTTTTG-3' (SEQ ID NO:11); 3R: 5'-CAACTATATTTGGAATTGCTATAC-3' (SEQ ID NO:12); 4F: 5'-TGATGTTATGATTTTTTCTTTTTCT-3' (SEQ ID NO:13); 4R: 5'-CAATTCTTCAAAGTATGAAGTCA-3' (SEQ ID NO:14). Primer 1F and 4R are located in 5'- and 3'-untranslated regions in exons 1 and 4, respectively. The other primers are designed from intronic sequences. The amplicon sizes for exon 1, 2, 3, and 4 are 98 bp, 168 bp, 200 bp, and 224 bp, respectively. PCR amplifications of 50–100 ng of genomic DNA are performed in Techne PHC3 thermal cyclers using AmpliTaq Gold DNA polymerase enzyme (Perkin Elmer Cetus) with its commercial buffer (final $MgCl_2$ concentration is 1.5 mM). Amplification conditions are as follows: initial denaturation at 94° C. for 10 min., followed by 35 cycles of: 45 sec. denaturation at 94° C., 45 sec. annealing at 55° C., and 45 sec extension at 72° C.; and a final extension at 72° C. for 10 min. The amplicons are first visualized on a 1% Ethidium Bromide-stained agarose gel. SSCP analysis is performed using genomic DNA as described by Baysal et al. in Gene 217, 107 (1998). Aberrant amplicons are sequenced in an ABI377 fluorescent sequencer. Sequence data are analyzed using Sequencher software (Gene Codes Corporation) . The segregation of mutations in PGL families and their screening in normal control chromosomes are performed by restriction enzyme analyses of mutant amplicons. The mutations in PGL families result in loss of recognition site for the following restriction enzymes: family 3, NlaIII; family 5 and family 7, MspI; family 8, MboII; family 11, AvaII. All digestions are performed overnight with 5–10 fold enzyme excess following manufacturer's recommendations (New England Biolabs).

Germ-line mutations in SDHD were examined in five families (families 3, 5, 7, 8, and 11) who showed significant linkage to PGL1 and demonstrated distinct disease haplotypes. Using two affected/carrier individuals from each family, each exon and its splice sites were amplified by primers designed from the flanking intronic sequences.

Additionally, the single-step method of RNA extraction of Chomczynski and Sacchi, in Anal. Biochem. 162, 156 (1987) is used following a commercial protocol (RNAzol™ B, Tel-Test). cDNA synthesis is performed using SUPERSCRIPT II (Life Technologies) and oligo (dT) primers following the recommended conditions. RT-PCR of cDNA templates for allelic expression analysis is performed by 30 cycles of amplification with primers 1F and 4R (amplicon size is 533 bp) following the commercial protocol (Life Technologies). PCR products are precipitated with isopropanol and washed with 70% ethanol and resuspended in TE buffer to ensure optimum buffer conditions during later restriction enzyme digestion. A silent single nucleotide polymorphism (SNP), (C/T) in codon 68 in exon 3 is identified by SSCP and sequence analyses in family 8 and in several fetal samples. This SNP, detected by SpeI restriction digestion is used for allelic expression analysis in the tissues. The bi-allelic expression pattern (FIG. 4) is confirmed in an independent experiment, where 27 cycles of PCR amplification is employed.

Each amplicon was then analyzed by Single Strand Conformational Polymorphism (SSCP). The SSCP analysis yielded at least one aberrant conformer cosegregating with the disease chromosome in each family. While Families 5 and 7 had the same aberrant conformer, Family 3 had a distinct aberrant conformer in exon 3. Family 11 had an aberrant conformer in exon 2. Family 8 showed distinct, aberrant conformers in exons 2 and 3.

Direct sequencing of each amplicon revealed the sequence alteration responsible for the SSCP conformers as shown in FIG. 2. Families 8 and 11 have nonsense mutations at codon 36 and codon 38, respectively, creating premature stop codons. Both stop codons are located within the mitochondrial signal peptide, and presumably block production of mature cybS. Family 3 has a missense mutation, changing Histidine residue 102 to Leucine. Families 5 and 7 have a missense mutation that changes Proline residue 81 to Leucine. We previously described extensive haplotype sharing among Families 12, 24, and 26. These families also show extensive haplotype sharing with Family 7 and, as expected, they all have the same missense mutation.

FIG. 3 is an alignment of cybS amino acid sequences from four eukaryotic multicellular organisms identified by BLASTP analysis of Swissprot database. The alignment reveals conserved amino acids denoted by stars (Clustal W 1.7). The numbers in FIG. 2 indicate the mutated amino acids (in bold) in PGL families. The amino acids whose codons span exon-exon boundaries in human genomic sequence are underlined. The vertical arrow denotes the amino terminal of mature peptide. All of the missense mutations characterized to date replace amino acids which are conserved in four eukaryotic multicellular organisms characterized to date. Histidine residue 102 is located in a region thought to harbor an axial ligand form of heme in the E. coli enzyme. The other two missense mutations result in nonconservative amino acid substitutions that could dramatically alter cybs conformation. None of the mutations has been observed in more than 200 normal control chromosomes analyzed to date. The mutations perfectly co-segregate with the disease phenotype in all affected individuals. The mutations are also inherited in a Mendelian fashion by all at-risk (paternal inheritance) and not-at risk (imprinted maternal inheritance) carrier individuals as identified by haplotype analysis.

Figure 4A:
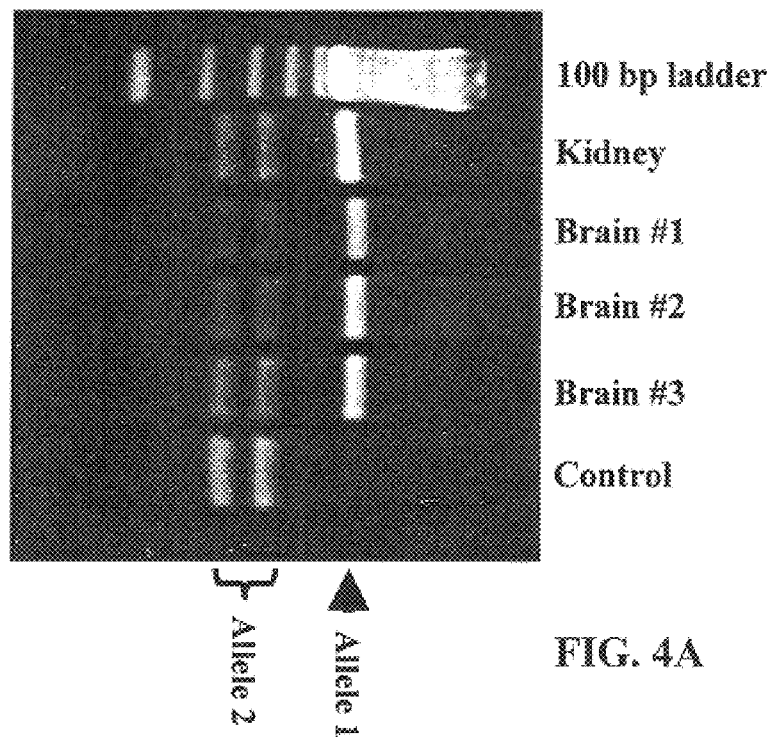
FIGS. 4A and 4B show bi-allelic expression of SDHD.
Figure 4B:
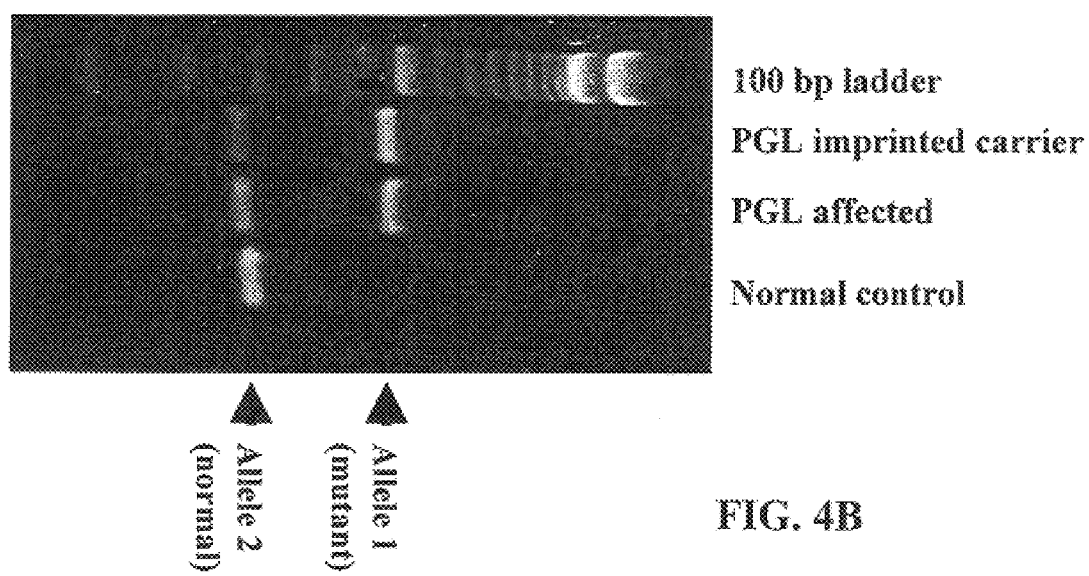

Allele specific expression of SDHD was assessed to determine whether the lack of maternal disease transmission in PGL1 is caused by paternal mono-allelic imprinted expression. Bi-allelic expression was detected in lymphoblastoid cell lines from affected and imprinted carrier individuals and in adult brain tissues as well as in fetal tissue from brain and kidney. FIGS. 4A and 4B shows bi-allelic expression of SDHD. FIG. 4A includes three independent brain samples and one kidney sample which show expression of both SDHD alleles as detected by RT-PCR-restriction digestion (SpeI) analysis. A homozygous brain sample is included in the last lane as a control for restriction digestion. In FIG. 4B lymphoblastoid cell lines from both PGL affected and imprinted carriers show bi-allelic expression. The mutation in family 5 is used for RT-PCR-restriction digestion analysis (MspI). A lymphoblastoid cell line from a normal individual is included in the last lane as a control for restriction digestion. Thus, these results cannot explain why children of affected mothers fail to develop PGL. Unlike most endogenously imprinted genes, SDHD is not located in an imprinted genomic domain. This observation has prompted the hypothesis that PGL1 mutations cause ectopic imprinting. Given the single base pair mutations in SDHD and its bi-allelic expression in lymphoblastoid cells from affected and imprinted individuals, this hypothesis seems unlikely. Although the precise mechanism of the imprinted inheritance pattern in PGL1 remains to be determined, mono-allelic expression of SDHD may be confined to the CB and other paraganglionic cells, similar to the brain-limited imprinting of UBE3A of Angelman syndrome.

Tumors from PGL1 families often show loss of heterozygosity with exclusive loss of normal maternal chromosome at 11q23. Germ-line loss-of function mutations in the paternal alleles and subsequent somatic loss of normal maternal alleles suggest that SDHD functions as a tumor-suppressor gene at the cellular level, subject to two-hit inactivation.

PGL is unusual among hereditary tumor syndromes characterized to date in that the defective gene encodes a mitochondrial protein. Candidate genes located on human chromosome 11q23 were defined by genetic recombination events in PGL families. There are several novel and unexpected features of these results including: this is the first hereditary tumor caused by germ-line defects in a gene encoding a mitochondrial protein; the properties of the mutant protein strongly suggest that the defective mitochondrial complex is an oxygen sensor; and this model for oxygen sensing provides direct evidence that continuous hypoxic stimulation can lead to tumor development.

Thus, it appears that PGL1 may be a critical component in the oxygen sensing and signaling pathway. Based on the phenotypic similarity between PGL and the CB's response to chronic hypoxia, it appears that cybS will be a critical component of the oxygen-sensing system of paraganglionic tissue. Consequently, its loss could lead to chronic hypoxic stimulation and cellular proliferation.

Polynucleotides of the present invention may be produced in large amounts by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are well known in the art. The polynucleotides of the present invention may also be produced by any number of chemical synthesis means commonly known in the art.

Polynucleotide constructs prepared for introduction into a prokaryotic or eukaryotic host may comprise a replication system recognized by the host, including the intended polynucleotide fragment encoding the desired polypeptide, and will preferably also include transcription and translation initiation regulatory sequences operably linked to the polypeptide encoding segment. Expression vectors for creating expression systems may include, for example, an origin of replication or a replicon or an autonomously replicating sequence (ARS), as well as expression control sequences, such as a promoter, or an enhancer and necessary processing information sites, such as ribosome-binding sites, RNA splice sites, polyadenylation sites, transcriptional terminator sequences, and mRNA stabilizing sequences. Secretion signals may also be included where appropriate which allow the protein to cross and/or lodge in cell membranes or be secreted from the cell. Such replicative cloning vectors may be prepared by means of standard recombinant techniques well known in the art.

"Regulatory sequences" is a term which refers to sequences normally within 10 Kb of the coding region of a locus which affect the expression of the gene (including transcription of the gene, and translation, splicing, stability or the like of the messenger RNA).

The selection of an appropriate promoter and other necessary vector sequences will be selected so as to be functional in the host, and preferably include, when appropriate, those naturally associated with SDHD genes, for example. Examples of workable combinations of cell lines and expression vectors are known in the art. Promoters such as the trp, lac, and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described and known in the art. Appropriate non-mammalian promoters might include the early and late promoters from SV40 or promoters derived from murine moloney leukemia virus, mouse tumor virus, avian sarcoma viruses, adenovirus II, bovine papilloma virus or polyoma. In addition, the construct may be joined to an amplifiable gene (such as DHFR) so that multiple copies of the gene may be made. Appropriate enhancer and other expression control sequences are known in the art.

While such expression vectors may replicate autonomously, they may also replicate by being inserted into the genome of the host cell, thus creating a recombinant host cell, by methods known in the art.

Additionally, vectors containing the nucleic acids of interest can be transcribed in vitro, and the resulting RNA introduced into the host cell by known methods, e.g., by injection, or the vectors can be introduced directly into host cells by methods well-known in the art, which vary depending on the type of cellular host, including electroporation, transfection employing calcium chloride, rubidium chloride, calcium phosphate, DEAE-dextran, or other substances; microprojectile bombardment; lipofection; infection (where the vector is an a infectious agent, such as a retroviral genome. Introduction of polynucleotides into a host cell by any method known in the art, including those described above, will be referred to as "transformation."

Prokaryotic or eukaryotic cells transformed with the polynucleotides of the present invention will be useful not only for the production of the nucleic acids and polypeptides of the present invention, but also, for example, in studying the characteristics of mitochondrial complex II, including but not limited to the cybS proteins.

A nucleic acid which is not naturally occurring, referred to herein as "recombinant nucleic acid," is understood to mean a nucleic acid which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

Polynucleotide polymorphisms or mutations associated with PGL1 alleles which predispose to PGL or are associated with pathogenic hypoxic events can be detected by hybridization with a polynucleotide probe which forms a stable hybrid with that of a target sequence, under stringent to moderately stringent hybridization and wash conditions. The SDHD mutations characterized to date are shown in FIG. 2 and are described in detail above. Stringent conditions will be used for situations where the probe is expected to be perfectly complementary to the target sequence. Hybridization stringency may be lessened if some mismatching is expected, for example, if variants are expected with the result that the probe will not be completely complementary. Conditions are chosen which rule out nonspecific/adventitious bindings, that is which minimize noise or background.

Probes for SDHD alleles may be derived from the sequences of the SDHD region (PGL1) or its cDNAs. The probes may be of any suitable length, which span all or a portion of the SDHD (PGL1) region, and which allow specific hybridization to the SDHD region. The probes will include an isolated polynucleotide attached to a label or reporter molecule and may be used to isolate other polynucleotide sequences, having sequence similarity by standard methods. There are numerous techniques for preparing and labeling probes. Examples of some standard techniques can be found in Sambrook et al., 1989, and Ausubel et al., 1992 both of which are hereby incorporated herein in their entirety by reference. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single-or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about fifteen nucleotides, and fewer than about 6 Kb, usually fewer than about 1.0 Kb, from a polynucleotide sequence encoding SDHD are preferred as probes. The probes may also be used to determine whether mRNA encoding SDHD is present in a cell or tissue. "Protein modifications or fragments" are provided by the present invention for mitochondrial complex II (e.g., the cybS portion of mitochondrial complex II) polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{32}P$, ligands, which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. There are numerous methods of labeling polypeptides and these methods are well known in the art.

"Protein purification" refers to various methods for the isolation of polypeptides, e.g. cybS polypeptides, from other biological material, such as from cells transformed with recombinant nucleic acids encoding the polypeptides (e.g. cybS polypeptides), and are well known in the art. For example, such polypeptides may be purified by immunoaffinity chromatography employing, e.g., the antibodies provided by the present invention. Various methods of protein purification are well known in the art, and include those described in Scopes, 1982, which is hereby incorporated herein in its entirety by reference.

A polypeptide produced as an expression product of an isolated and manipulated genetic sequence is referred to as an "isolated polypeptide," as used herein, even if expressed in a homologous cell type. Synthetically made forms or molecules expressed by heterologous cells are inherently isolated molecules.

It is further contemplated within the scope of this invention that SDHD mutations will be detected using nucleic acid probe assays which will employ recently developed nucleic acid microchip technology. This technology utilizes an array of many thousands of probes bound to a chip to analyze a sample. This method thus analyzes a sample simultaneously using all the probes which are bound to the microchip.

Antisense polynucleotide sequences will be useful in preventing or diminishing the expression of the SDHD locus, which will be desirable either for experimental or therapeutic purposes. For example, polynucleotide vectors containing all or a portion of the SDHD locus or other sequences from the PGL1 region (particularly those flanking the PGL1 locus) may be placed under the control of a promoter in an antisense orientation and introduced into a cell. Expression of such an antisense construct within a cell will interfere with SDHD transcription and/or translation and/or replication.

The present invention broadly contemplates a method of supplying wild-type mitochondrial complex II genes, specifically SDHD gene (or a functional cybS protein) to a cell which carries mutant mitochondrial complex II alleles, specifically, SDHD alleles. It is expected that supplying such a function to the affected cells would suppress neoplastic growth of the recipient cells alone or in combination with hyperbaric treatment. The wild-type SDHD gene or a part of the gene may be introduced into the cell in a vector such that the gene remains extrachromosomal. In such a situation, the gene will be expressed by the cell from the extrachromosomal location. If a gene portion is introduced and expressed in a cell carrying a mutant SDHD allele, the gene portion should encode a part of the cybS protein which is required for non-neoplastic cell-growth. More preferred is the situation where the wild-type SDHD gene or a part thereof is introduced into the mutant cell in such a way that it recombines with the endogenous mutant SDHD gene present in the cell. Such recombination requires a double recombination event which results in the correction of the SDHD gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art. Cells transformed with the wild-type SDHD gene can be used as model systems to study cancer remission and drug treatments which promote such remission.

The SDHD gene or fragment, may be utilized in gene therapy methods in order to increase the amount of the expression products of such genes in cancer cells. Such gene therapy can be particularly appropriate for use in both cancerous and pre-cancerous cells, in which the level of cybS is absent or diminished compared to normal cells. It may also be useful to increase the level of expression of a given SDHD gene even in those tumor cells in which the mutant gene is expressed at a "normal" level, but the gene product is not fully functional.

Gene therapy would be carried out according to generally accepted methods, for example, as described by Friedman in *Therapy for Genetic Disease*, T. Friedman, ed., Oxford University Press (1991), pp. 105–121, hereby incorporated herein in its entirety by reference. Cells from a patient's tumor may be first analyzed by the diagnostic methods described above, to ascertain the production of cybS in the tumor cells. A virus or plasmid vector, containing a copy of the SDHD gene linked to expression control elements and capable of replicating inside tumor cells, may then be prepared. Suitable vectors are known in the art. The vector is then injected into the patient, either locally at the site of the tumor, or systemically to reach tumor cells that may have metastasized to other sites. If the transfected gene is not permanently incorporated into the genome of each of the targeted tumor cells, the treatment may have to be repeated periodically.

Oxidative stress appears to play a role in many neurodegenerative diseases, including Parkinson's disease. One manifestation of this disease state is an increase in reactive oxygen species in the brain and in some cases peripheral tissue. Specifically, there is growing evidence that oxidative stress and mitochondrial respiratory failure play roles in nigral neuronal death in Parkinson's disease. Cells that are exposed to oxidative stress are subjected to elevated levels of one or more reactive oxygen species including superoxide, hydroxyl radicals, tyrosyl radicals, and reactive nitrogen species, such as peroxynitrate. Exposure of neuronal cells to these reactive oxygen species may be at least partially responsible for the neurotoxicity in some neurodegenerative diseases such as Parkinson's disease. The presence of excess reactive oxygen species may be a result of dysfunctional oxygen sensors from the mitochondrial complex II family, such as cybS. Thus, augmenting oxygen sensing in oxidatively stressed cells by treatment with an oxygen sensor protein from mitochondrial complex II may alleviate the pathogenic conditions of Parkinson's disease and potentially other neurodegenerative diseases.

Preliminary studies indicate that autologous carotid body transplants may prove useful to replace damaged neurons in the midbrain in substantia nigra in Parkinson's disease. The CB cells can replace the missing or defective neurons and provide an abundant source of dopamine, the deficient hormone in Parkinson's disease. The assessment and the manipulation of the proliferative and oxygen-sensing capabilities of CB cells prior to the transplantation may prove useful for predicting and altering the CB cells' long-term biological behavior in ectopic locations such as the stnatum inside the- brain. These assessments/manipulations can now be easily performed by testing or altering SDHD and/or its protein product.

The present findings also provide insight into an alternative aspect of the present invention; methylation. The DNA template from human cancer cells often displays somatic changes in DNA methylation. However, the precise role of abnormal DNA methylation in human tumorigenesis has not been established. DNA methylases transfer methyl groups from the universal methyl donor S-adenosyl methionine to specific sites on the DNA. Several biological functions have been attributed to the methylated bases in DNA. The most established biological function for specific DNA methylation is for the protection of DNA from digestion by cognate restriction enzymes. The restriction modification phenomenon has, to date, been observed only in bacteria. Mammalian cells, however, possess a different methylase that exclusively methylates cytosine residues that are 5' neighbors of guanine (CpG). This methylation has been shown by several lines of evidence to play a role in gene activity, cell differentiation, tumorigenesis, X-chromosome inactivation, genomic imprinting and other major biological processes.

CpG islands, discrete regions of CpG dinucleotides, remain unmethylated in normal cells, except during X-chromosome inactivation and parental specific imprinting. This methylation of 5' regulatory regions can lead to transcriptional repression. These CpG islands have recently been identified on a number of chromosomes which are aberrantly hypermethylated in numerous types of human cancers. This process of silencing gene transcription has been implicated as an alternative mechanism to mutations of coding regions for inactivation of tumor suppressor genes. For example, this change (hypermethylation of the promoter region) has now been associated with the loss of expression of several genes including VHL, a renal cancer tumor suppressor gene on 3p, the estrogen receptor gene on 6q, and the H19 gene on 11p.

It is likely that imprinting of the SDHD gene is a determining factor in progression of tumor growth in PGL. Therefore, it would be desirable to either prevent the imprinting in the male carrier of PGL, or to supply a form of the SDHD gene that does not get methylated for therapeutic treatment. There are circumstances where it will be beneficial to use an expression system of the present invention wherein said DNA sequence includes a nucleotide analog which is incapable of being methylated. Additionally, it may be beneficial to supply this same non-methylatable form of SDHD in order to restore oxygen sensing under a variety of hypoxic conditions including other cancers, for treatment of stroke or treatment of heart disease.

Similarly, when a neoplasm or tumor is associated with a defect in the SDHD gene, it may be helpful to use methylation suppressive reagents such as 5-azacytadine, a cytosine analog which cannot be methylated, which can be introduced to a cell. There are numerous DNA demethylases known in the art, any of which could be specifically targeted to cells defective in cybS in order to remove methylation from the affected SDHD gene.

The polynucleotide sequences used in the method of the invention may be the native, unmethylated sequence or, alternatively, may be a sequence in which a nonmethylatable analog is substituted within the sequence. Preferably, the analog is a nonmethylatable analog of cytidine, such as 5-azacytadine. Other analogs will be known to those of skill in the art. Alternatively, such nonmethylatable analogs could be administered to a subject as drug therapy, alone or simultaneously with a sense structural gene for SDHD or sense promoter for SDHD operably linked to the SDHD structural gene.

It is possible that a decreased level of SDHD transcription may be the result of hypermethylation of the SDHD gene or its promoter region. It is often desirable to determine whether the gene in question is hypermethylated. In particular, the cytosine rich areas, the CpG islands, which usually lie in the 5' regulatory regions of genes are normally unmethylated. The term "hypermethylation" includes any methylation of cytosine which is normally unmethylated in the SDHD gene sequence and can be detected by restriction endonuclease treatment of the SDHD gene and Southern blot analysis. Restriction endonuclease analysis is an example of one method to detect hypermethylation of the SDHD gene. Any restriction enzyme that includes CG as part of its recognition site and that is inhibited when the C is methylated, can be utilized. Methylation sensitive restriction endonucleases such as BssHII, MspI, NotI or HpaII, used alone or in combination are examples of such endonucleases. Other methylation sensitive restriction endonucleases will be known to those skilled in the art. Additionally, PCR and other methods known in the art can be used to detect the methylation status of the SDHD gene.

Rational drug design is also facilitated by the present invention. The goal of rational drug design is to produce structural analogs of a particular biologically active polypeptide or of small molecules with which they interact (e.g., agonists, antagonists, inhibitors or enhancers) in order to design drugs which are more active or more stable forms of the original polypeptide. These analogs may also enhance or interfere with the function of a polypeptide in vivo. In some cases, determining the three dimensional structure (by x-ray crystallography or computer program modeling, or by analogy to that of a homologous protein) can reveal important information about the protein's catalytic residues. HIV protease inhibitors are examples of rationally designed drugs. Experiments utilizing the technique of alanine scanning mutagenesis described by Wells et al. 1991, hereby incorporated herein in its entirety by reference, can provide additional or confirming data about the functional amino acids of a protein. This detailed information about the protein of interest can allow one to design drugs which have improved cybS activity or stability, or which may act as enhancers, inhibitors, agonists, or antagonists of cybS's activity. The cloned SDHD gene (or additional cloned genes from the mitochondrial complex II) will allow for sufficient cybS peptide (or other mitochondrial complex II peptide) to be produced for these x-ray crystallographic studies. Additionally, the knowledge of the cybS protein sequence provided herein will be useful to those employing computer modeling techniques for delineating the protein's 3-dimensional structure.

Although the majority of this disclosure is directed to establishing or restoring an oxygen sensor, under certain circumstances, it may be beneficial to create cells which are tolerant of hypoxic conditions by creating an SDHD knock-out mutation. For example, synthetic tissue or bone replacement therapy is often dependent upon diffusion of nutrients to cells within a synthetic matrix. The success of these tissue implants is often dependent upon formation or implantation of new blood vessels to this synthetic tissue. The blood vessels carry essential nutrients including oxygen to the tissue. Often, blood vessels fail to grow to a depth of greater than 100 nm, thus shutting off the center of the matrix from essential nutrients and often resulting in death of the tissue. Creating a population of cells which require less oxygen and/or nutrients while remaining viable may increase the success of tissue replacement and similar therapy.

While the foregoing has been set forth in considerable detail, the sequences are presented for elucidation, and not limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concept described herein.

What is claimed is:

1. An expression system comprising a recombinant host cell transformed with SEQ ID NO:2 operably linked to a promoter.

2. The expression system of claim 1, wherein the recombinant host cell is selected from the group consisting of yeast, bacteria, mammalian cells, and plant cells.

3. The expression system of claim 1, wherein the promoter is selected from the group consisting of a metallothionein promoter, a 3-phosphoglycerate kinase promoter, an enolase promoter, a glyceraldehydes-3-phosphate dehydrogenase promoter, a early promoter from SV40, a late promoter from SV40, a promoter from murine moloney leukemia virus, a promoter from mouse tumor virus, a promoter from avian sarcoma virus, a promoter from adenovirus 11, and a promoter from bovine papilloma virus.

4. An isolated DNA sequence comprising SEQ ID NO:2.

5. The isolated DNA sequence of claim 4, further comprising a detectable label.

6. An isolated DNA sequence comprising SEQ ID NO:1, wherein said sequence includes a mutation in SEQ ID NO:1 selected from the group consisting of:

a T at nucleotide base number 106 of SEQ ID NO:1;
a T at nucleotide base number 112 of SEQ ID NO:1;
a T at nucleotide base number 242 of SEQ ID NO:1; and
a T at nucleotide base number 305 of SEQ ID NO:1.

7. The isolated DNA sequence of claim 6, further comprising a detectable label.

8. An isolated DNA sequence comprising the complementary strand of SEQ ID NO:2 or SEQ ID NO:1, wherein SEQ ID NO:1 includes a mutation selected from the group consisting of:

a T at nucleotide base number 106 of SEQ ID NO:1;
a T at nucleotide base number 112 of SEQ ID NO:1;
a T at nucleotide base number 242 of SEQ ID NO:1; and
a T at nucleotide base number 305 of SEQ ID NO:1.

9. The isolated DNA sequence of claim 8, further comprising a detectable label.

* * * * *

UNITED STATES PATENT AND TRADEMARK OFFICE
CERTIFICATE OF CORRECTION

PATENT NO. : 6,468,789 B1  Page 1 of 1
DATED : October 22, 2002
INVENTOR(S) : Baysal et al.

It is certified that error appears in the above-identified patent and that said Letters Patent is hereby corrected as shown below:

Column 3,
Line 9, after "of" delete "PGLL" and substitute -- PGL1 -- therefor.

Column 7,
Interchange the paragraph beginning on line 29 and ending on line 65 with the paragraph beginning on line 66 and ending on column 8, line 4.

Column 14,
Line 18, after "the" delete "stnatum" and substitute -- striatum --

Column 25,
Line 58, after "adenovirus" delete "11" and substitute -- II -- therefor.

Signed and Sealed this

Fourteenth Day of September, 2004

JON W. DUDAS
*Director of the United States Patent and Trademark Office*

SEQUENCE LISTING

```
<160> NUMBER OF SEQ ID NOS: 18

<210> SEQ ID NO 1
<211> LENGTH: 480
<212> TYPE: DNA
<213> ORGANISM: Homo sapiens

<400> SEQUENCE: 1
atggcggttc tctggaggct gagtgccgtt tgcggtgccc taggaggccg agctctgttg      60
cttcgaactc cagtggtcag acctgctcat atctcagcat ttcttcagga ccgacctatc     120
ccagaatggt gtggagtgca gcacatacac ttgtcaccga gccaccattc tggctccaag     180
```

```
gctgcatctc tccactggac tagcgagagg gttgtcagtg ttttgctcct gggtctgctt      240
ccggctgctt atttgaatcc ttgctctgcg atggactatt ccctggctgc agccctcact      300
cttcatggtc actggggcct tggacaagtt gttactgact atgttcatgg ggatgccttg      360
cagaaagctg ccaaggcagg cttttggca cttttcagctt taacctttgc tgggctttgc      420
tatttcaact atcacgatgt gggcatctgc aaagctgttg ccatgctgtg aagctctga       480
```

<210> SEQ ID NO 2
<211> LENGTH: 1333
<212> TYPE: DNA
<213> ORGANISM: Homo sapiens

<400> SEQUENCE: 2

```
gttggtggat gaccttgagc cctcaggaac gagatggcgg ttctctggag gctgagtgcc       60
gtttgcggtg ccctaggagg ccgagctctg ttgcttcgaa ctccagtggt cagacctgct      120
catatctcag catttcttca ggaccgacct atcccagaat ggtgtggagt gcagcacata      180
cacttgtcac cgagccacca ttctggctcc aaggctgcat ctctccactg gactagcgag      240
agggttgtca gtgttttgct cctgggtctg cttccggctg cttatttgaa tccttgctct      300
gcgatggact attccctggc tgcagccctc actcttcatg gtcactgggg ccttggacaa      360
gttgttactg actatgttca tggggatgcc ttgcagaaag ctgccaaggc agggcttttg      420
gcactttcag ctttaacctt tgctgggctt tgctatttca actatcacga tgtgggcatc      480
tgcaaagctg ttgccatgct gtggaagctc tgaccttttt gacttcatac tttgaagaat      540
tgatgtatgc ctcttttgcct ctgctttgtc atgccattaa gctcacaata aggaagaaat      600
aacagataag tccattggtg acagccttc ttctcttaat cacaagatta ttcagaattt      660
aatctttgag gaaaaggttt gagaggaatt atatctaagt tgtgagactg agttctatat      720
tctggtgagt taatggggtt gcctcccagc ttcttataag actcacagta taactaaaca      780
tgatatatca gcttttgcct ttcaatttat caatctctta aagagaatcc aactttatta      840
cgattagtat atgatcaaac ttccatattt gccttgggaa taatggacaa agggaaatac      900
tcttaattca tgaataaaaa ctttgcagaa aattagacag tgtttaattt tcgaaaactt      960
ccctctctag acagtagata ccacctactg atggttacat atactaggga aattttaaaa     1020
ttaggaaatg ctgatagctc atattataaa tttctaaatc ctaggaagaa acgcttggag     1080
tgcttctgaa tatacagaag ttccatttaa gggcaagttt ccccgtagat gtatcaaaat     1140
actaccaact gtaaattgag atttaattcc caaatgtatt ctacttgttc taaaacaatc     1200
tgtccacaaa tataaaacta taagtaataa attgttattt tcgcacaatg gaatctcta      1260 atgtgaaaat gtattctatg aaaataattt tttaataaa atgttatata ataaagtgt       1320 cttctatgct ttt                                                         1333
```

<210> SEQ ID NO 3
<211> LENGTH: 159
<212> TYPE: PRT
<213> ORGANISM: Homo sapiens

<400> SEQUENCE: 3

```
Met Ala Val Leu Trp Arg Leu Ser Ala Val Cys Gly Ala Leu Gly Gly
1               5                   10                  15

Arg Ala Leu Leu Leu Arg Thr Pro Val Val Arg Pro Ala His Ile Ser
            20                  25                  30
```

-continued

```
Ala Phe Leu Gln Asp Arg Pro Ile Pro Glu Trp Cys Gly Val Gln His
             35                  40                  45
Ile His Leu Ser Pro Ser His His Ser Gly Ser Lys Ala Ala Ser Leu
 50                  55                  60
His Trp Thr Ser Glu Arg Val Val Ser Val Leu Leu Gly Leu Leu
 65                  70                  75                  80
Pro Ala Ala Tyr Leu Asn Pro Cys Ser Ala Met Asp Tyr Ser Leu Ala
                 85                  90                  95
Ala Ala Leu Thr Leu His Gly His Trp Gly Leu Gly Gln Val Val Thr
            100                 105                 110
Asp Tyr Val His Gly Asp Ala Leu Gln Lys Ala Ala Lys Ala Gly Leu
            115                 120                 125
Leu Ala Leu Ser Ala Leu Thr Phe Ala Gly Leu Cys Tyr Phe Asn Tyr
130                 135                 140
His Asp Val Gly Ile Cys Leu Ala Val Ala Met Leu Trp Lys Leu
145                 150                 155
```

<210> SEQ ID NO 4
<211> LENGTH: 20
<212> TYPE: DNA
<213> ORGANISM: Homo sapiens

<400> SEQUENCE: 4
aaacgcagca agaccctgtt                                              20

<210> SEQ ID NO 5
<211> LENGTH: 20
<212> TYPE: DNA
<213> ORGANISM: Homo sapiens

<400> SEQUENCE: 5 agggttcat gaccatccta                                               20

<210> SEQ ID NO 6
<211> LENGTH: 20
<212> TYPE: DNA
<213> ORGANISM: Homo sapiens

<400> SEQUENCE: 6
catttgtcca gttacccgta                                              20

<210> SEQ ID NO 7
<211> LENGTH: 21
<212> TYPE: DNA
<213> ORGANISM: Homo sapiens

<400> SEQUENCE: 7
attgactaat ggacactgga a                                            21

<210> SEQ ID NO 8
<211> LENGTH: 19
<212> TYPE: DNA
<213> ORGANISM: Homo sapiens

<400> SEQUENCE: 8
tcagggtggg aagacccct                                               19

<210> SEQ ID NO 9
<211> LENGTH: 22
<212> TYPE: DNA
<213> ORGANISM: Homo sapiens

<400> SEQUENCE: 9
gatcatccta atgactcttt cc                                        22

<210> SEQ ID NO 10
<211> LENGTH: 20
<212> TYPE: DNA
<213> ORGANISM: Homo sapiens

<400> SEQUENCE: 10
agcagcagcg atggagagaa                                           20

<210> SEQ ID NO 11
<211> LENGTH: 24
<212> TYPE: DNA
<213> ORGANISM: Homo sapiens

<400> SEQUENCE: 11
cttttatgaa tctggtcctt tttg                                      24

<210> SEQ ID NO 12
<211> LENGTH: 24
<212> TYPE: DNA
<213> ORGANISM: Homo sapiens

<400> SEQUENCE: 12
cttttatgaa tctggtcctt tttg                                      24

<210> SEQ ID NO 13
<211> LENGTH: 25
<212> TYPE: DNA
<213> ORGANISM: Homo sapiens

<400> SEQUENCE: 13
tgatgttatg attttttctt tttct                                     25

<210> SEQ ID NO 14
<211> LENGTH: 23
<212> TYPE: DNA
<213> ORGANISM: Homo sapiens

<400> SEQUENCE: 14
caattcttca aagtatgaag tca                                       23

<210> SEQ ID NO 15
<211> LENGTH: 159
<212> TYPE: PRT
<213> ORGANISM: Homo sapiens

<400> SEQUENCE: 15

Met Ala Val Leu Trp Arg Leu Ser Ala Val Cys Gly Ala Leu Gly Gly
 1               5                  10                  15

Arg Ala Leu Leu Leu Arg Thr Pro Val Val Arg Pro Ala His Ile Ser
                20                  25                  30

Ala Phe Leu Gln Asp Arg Pro Ile Pro Glu Trp Cys Gly Val Gln His
            35                  40                  45

Ile His Leu Ser Pro Ser His His Ser Gly Ser Lys Ala Ala Ser Leu
        50                  55                  60

His Trp Thr Ser Glu Arg Val Val Ser Val Leu Leu Gly Leu Leu
65                  70                  75                  80

Pro Ala Ala Tyr Leu Asn Pro Cys Ser Ala Met Asp Tyr Ser Leu Ala

```
                        85                  90                  95
Ala Ala Leu Thr Leu His Gly His Trp Gly Leu Gly Gln Val Val Thr
                100                 105                 110

Asp Tyr Val His Gly Asp Ala Leu Gln Lys Ala Lys Ala Gly Leu
        115                 120                 125

Leu Ala Leu Ser Ala Leu Thr Phe Ala Gly Leu Cys Tyr Phe Asn Tyr
    130                 135                 140

His Asp Val Gly Ile Cys Lys Ala Val Ala Met Leu Trp Lys Leu
145                 150                 155

<210> SEQ ID NO 16
<211> LENGTH: 158
<212> TYPE: PRT
<213> ORGANISM: Bos taurus

<400> SEQUENCE: 16

Met Ala Leu Trp Arg Leu Ser Val Leu Cys Gly Ala Lys Glu Gly Arg
1               5                   10                  15

Ala Leu Phe Leu Arg Thr Pro Val Arg Pro Ala Leu Val Ser Ala
            20                  25                  30

Phe Leu Gln Asp Arg Pro Ala Gln Gly Trp Cys Gly Thr Gln His Ile
        35                  40                  45

His Leu Ser Pro Ser His His Ser Gly Ser Lys Ala Ala Ser Leu His
    50                  55                  60

Trp Thr Gly Glu Arg Val Val Ser Val Leu Leu Gly Leu Ile Pro
65                  70                  75                  80

Ala Ala Tyr Leu Asn Pro Cys Ser Ala Met Asp Tyr Ser Leu Ala Ala
                85                  90                  95

Thr Leu Thr Leu His Ser His Trp Gly Ile Gly Gln Val Val Thr Asp
                100                 105                 110

Tyr Val His Gly Asp Ala Val Gln Lys Ala Ala Lys Thr Gly Leu Leu
        115                 120                 125

Val Leu Ser Ala Phe Thr Phe Ala Gly Leu Cys Tyr Phe Asn Tyr His
    130                 135                 140

Asp Val Gly Ile Cys Lys Ala Val Ala Met Leu Trp Lys Leu
145                 150                 155

<210> SEQ ID NO 17
<211> LENGTH: 156
<212> TYPE: PRT
<213> ORGANISM: Ascaris suum

<400> SEQUENCE: 17

Met Leu Ser Ala Val Arg Arg Ala Ile Pro Leu Ser Ala Arg Ile Leu
1               5                   10                  15

Arg Thr Ser Leu Ile Gln Arg Cys Ala Gly Ala Thr Ser Ala Ala Val
            20                  25                  30

Thr Gly Ala Ala Pro Pro Gln Phe Asp Pro Ile Ala Ala Glu Lys Gly
        35                  40                  45

Phe Lys Pro Leu His Ser His Gly Thr Leu Phe Lys Ile Glu Arg Tyr
    50                  55                  60

Phe Ala Ala Ala Met Val Pro Leu Ile Pro Ala Tyr Phe Ile His
65                  70                  75                  80

Gly Arg Glu Met Asp Leu Cys Leu Ala Leu Ala Leu Thr Leu His Val
                85                  90                  95

His Trp Gly Val Trp Gly Val Val Asn Asp Tyr Gly Arg Pro Phe Val
```

-continued

```
              100                 105                 110
Leu Gly Asp Thr Leu Ala Ala Ala Val Arg Val Gly Ala Tyr Ile Phe
            115                 120                 125

Thr Ala Cys Leu Leu Ala Gly Leu Leu Tyr Phe Asn Glu His Asp Val
        130                 135                 140

Gly Leu Thr Arg Ala Phe Glu Met Val Trp Glu Leu
145                 150                 155
```

<210> SEQ ID NO 18
<211> LENGTH: 145
<212> TYPE: PRT
<213> ORGANISM: Caenorhabditis elegans

<400> SEQUENCE: 18

```
Met Ala Ala Ser Leu Arg His Met Ala His Phe Gln Lys Ala Leu Leu
1               5                   10                  15

Val Ala Arg Ser Ala Pro Arg Ile Ser Thr Ile Val Arg Ala Thr Ser
            20                  25                  30

Thr Leu Asn Asp Gly Ala Ser Lys Val Pro Asp His Ser Met His Phe
        35                  40                  45

Lys Leu Glu Arg Leu Trp Ala Val Gly Met Leu Pro Ile Leu Pro Ala
    50                  55                  60

Ser Tyr Phe Ile His Gly Pro Val Met Asp Ala Val Leu Thr Val Ala
65                  70                  75                  80

Leu Thr Leu His Ile His Trp Gly Ile His Gly Val Val Tyr Asp Tyr
                85                  90                  95

Ala Arg Pro Tyr Val Ile Gly Glu Ala Ala Ala Lys Ala Ala His Val
            100                 105                 110

Gly Val Tyr Leu Ile Thr Gly Leu Leu Leu Gly Ala Leu Leu His Phe
        115                 120                 125

Asn Thr Asn Asp Val Gly Ile Thr Lys Ala Phe Glu Leu Val Phe Ser
    130                 135                 140

Leu
145
```